Figure 19:
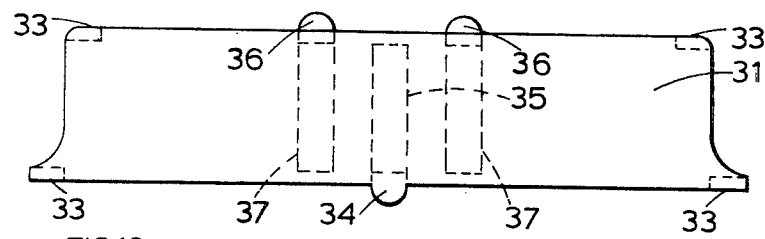

United States Patent [19]

Clarke

[11] 4,066,238
[45] Jan. 3, 1978

[54] MEANS FOR CONTROLLING FLUID FLOW

[76] Inventor: Ellis Whiteside Clarke, 47 Deramore Drive, Belfast, BT9 5JS, Northern Ireland

[21] Appl. No.: 650,360

[22] Filed: Jan. 19, 1976

[30] Foreign Application Priority Data

Jan. 17, 1975 United Kingdom ............... 2069/75

[51] Int. Cl.² ............................................. F16K 7/04
[52] U.S. Cl. ........................................... 251/6; 251/4; 251/7
[58] Field of Search ................. 251/4, 6–10, 251/342

[56] References Cited

U.S. PATENT DOCUMENTS

| 3,103,335 | 9/1963 | Martinez | 251/4 |
| 3,779,507 | 12/1973 | Clarke | 251/9 |

FOREIGN PATENT DOCUMENTS 36,527  11/1885  Germany ............................ 251/4

Primary Examiner—Martin P. Schwardron
Assistant Examiner—Richard Gerard
Attorney, Agent, or Firm—Scrivener, Parker, Scrivener & Clarke

[57] ABSTRACT

The invention provides means for controlling the flow of fluids such as parenteral fluids. It comprises a body and flexing means. The body defines a passageway with opposed flexible walls which can be held in contact throughout their cross-section except for a limited region of which the cross-section varies along the body. The limited region may be formed by tapered grooves in the walls. The flexing means retains the body flexed so that the walls thereof are held in contact over a localized area of limited axial length, due at least partly to the internal stresses set up in the body arising from its flexure. The body is movable lengthwise relative to the flexing means to alter the position of the localized area and thus to alter the rate of fluid flow through the body.

13 Claims, 29 Drawing Figures

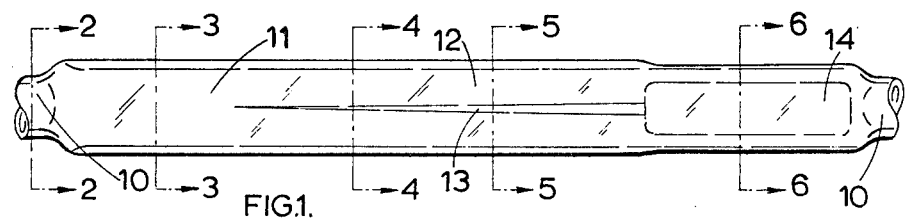

MEANS FOR CONTROLLING FLUID FLOW

This invention relates to means for controlling fluid flow. The development of the invention has been largely concerned with means for controlling the flow of liquids, but the invention may be applied to means for controlling the flow of gases.

The invention has been developed primarily with a view to providing means for controlling the flow of liquid materials such as blood and saline to patients undergoing medical treatment. In the administration of a liquid of that kind it is usual for a container containing a supply of the liquid to be suspended above the patient and for the liquid to flow to the patient through a tube provided with control means operative to determine the rate of flow of the liquid. The control means is usually adjustable so that the rate of flow of the liquid can be adjusted. For example the control means may be adjustable so as to permit the rate of flow to be varied to any desired value within a range of from 1 milliliter per hour to 400 milliliters per hour. The control means may also be such as to enable relatively unrestricted flow to occur through the tube; this is useful when the tube is to be flushed through and filled with liquid before the administration of liquid to the patient.

The means for controlling fluid flow which is the subject of the present invention is related to other means for that purpose which I have previously invented. In that previous invention the means for controlling fluid flow comprises a body defining a passageway having opposed flexible walls which for at least a portion of the axial length of the body are capable of being held in mutual contact throughout their cross-section except for a limited region, this region being of cross-section which varies along the general direction of flow through the passageway, with an externally applied clamp of which opposed jaws hold the walls in contact over a localised area of limited axial length, the point of action of the jaws being movable along the direction of flow to other positions to alter the position of the said area.

An important feature of the earlier invention is the provision of a clamp with opposed jaws operative to hold the walls of the body in contact over a localised area.

The present invention, however, is based on the discovery that the walls of the body can be caused to be retained in mutual contact by means other than an externally applied clamp.

According to the present invention there is provided means for controlling fluid flow comprising a body defining a passageway having opposed flexible walls which for at least a portion of the axial length of the body are capable of being retained in mutual contact throughout their cross-section except for a limited region, this region being of cross-section which varies along the general direction of flow through the passageway, and flexing means operative to retain the body in a flexed state such that the walls are held in contact, over a localised area of limited axial length, due at least partially to the internal stresses set up in the body arising from the flexure of the body rather than to external clamping forces applied to the opposite sides of the walls immediately adjacent to said area, the arrangement being such that the body can be moved lengthwise relative to the flexing means so as to alter the position of said area.

Thus the invention is based on the discovery that if the body is flexed to a certain shape the walls, over a localised area of limited axial length, can be held in mutual contact even in the absence of an externally applied clamp with jaws gripping the walls between them.

The body may be flexed in any of a number of different ways to achieve this contact of the walls over a localised area. For example it may be bent about a transverse axis at right-angles to the longitudinal axis of the passageway so that a kink is formed in the passageway. Alternatively the body may be bent about a transverse axis inclined at an angle other than a right-angle to the longitudinal axis of the passageway so that a kink is again formed, the kinked part of the body and the immediately adjacent parts of the body thus approximating in shape to part of a helix. In another alternative a short length of the body is twisted about the longitudinal axis of the body. For example a short length of the body may be twisted through 90° to about the longitudinal axis. Where the walls are twisted the internal stress in the walls retain the walls together.

The body may be such that in the absence of other forces the walls lie in mutual contact with each other, apart from in the limited region referred to. In that case the pressure of the fluid passing through the passageway, in use, must be greater than a certain minimum value, that is the pressure must be sufficient to force the walls apart, except in the localised area referred to, so as to ensure that in use the rate of flow is very largely determined by the cross-section of the limited region at that localised area. In a preferred arrangement, however, the body is such that in the absence of other forces the walls lie in mutually spaced relationship, and thus there is no longer the requirement for the pressure of the fluid to be greater than a certain minimum value to force the walls apart.

The limited region in which the walls do not come into contact is preferably formed by a groove in one of the walls or by complementary grooves in both of the walls of the body, the groove or each groove being of tapered form. Alternatively it would be possible for the region to be formed by the presence between the walls of a member of elongated, tapered shape. In the latter case, however, the member would normally have to be flexible, and difficulty might be encountered in locating the member in the passageway. The only exception to that would be where the body was twisted about its longitudinal axis, and the member lay along that axis; a rigid member could then be used.

At one end of the region referred to above the body may be formed with a closure portion having flexible walls capable of being retained in mutual contact throughout their entire cross-section, the arrangement being such that said localised area of limited axial length can be transferred to the closure portion whereupon the flow of fluid through the passageway ceases.

Alternatively or in addition the body may be formed with a free-flow portion having flexible walls which in use remain spaced apart even when the localised area of limited length is transferred to that free-flow portion.

The body preferably comprises a length of tube of a thermoplastic synthetic resin, flattened to form the opposed walls. The tube is preferably made of PVC, and may be transparent so that the operation of the flow control means can be observed.

One preferred form of flexing means, operative to cause the body to be flexed about an axis at least substantially at right-angles to the longitudinal axis of the passageway, comprises a principal abutment about which the body can be flexed in such a manner as to cause the walls adjacent to the abutment to be held in mutual contact, and formations which can engage the body on either side of the flexed portion and thus act to retain the body in its flexed state.

Figure 20:
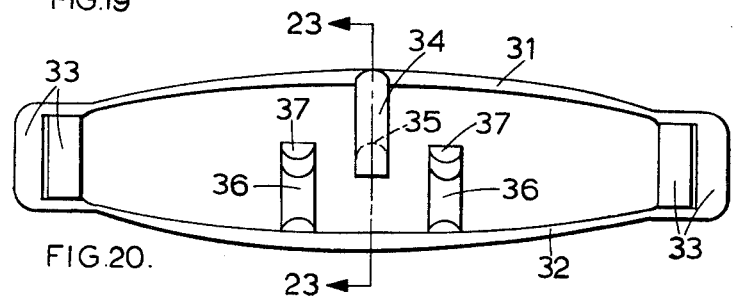
Figure 22:
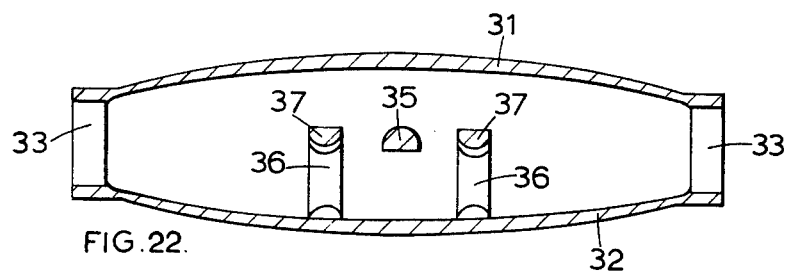
Figure 24:
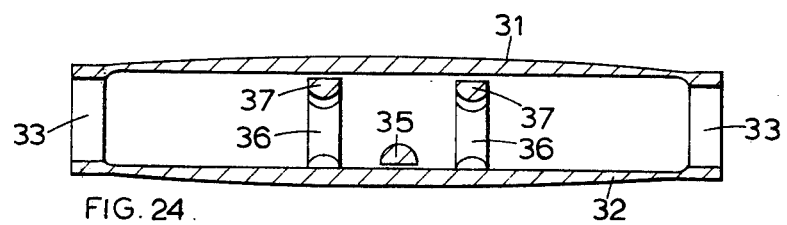
Figure 21:
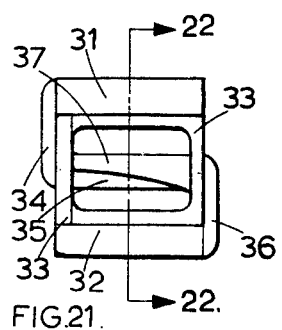
Figure 23:
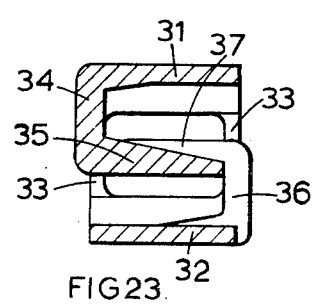
Figure 25:
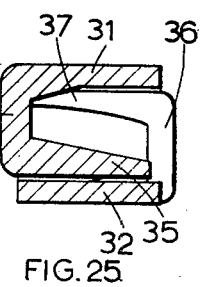
Figure 27:
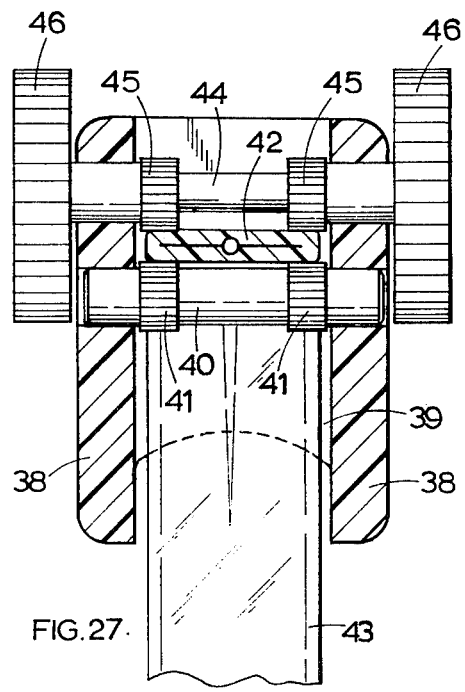
Figure 26:
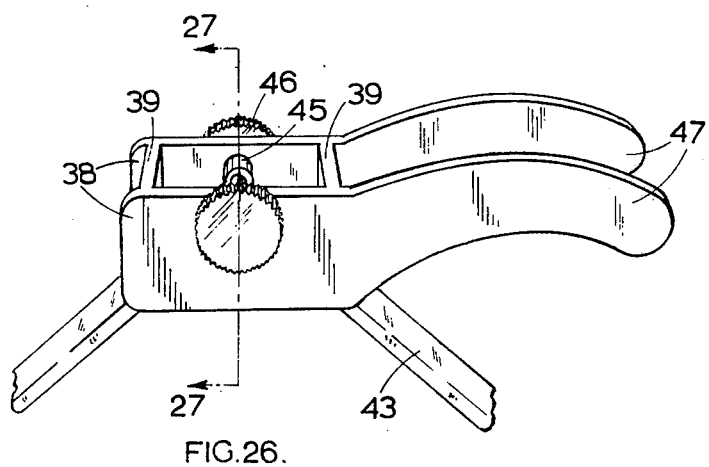
Figure 28:
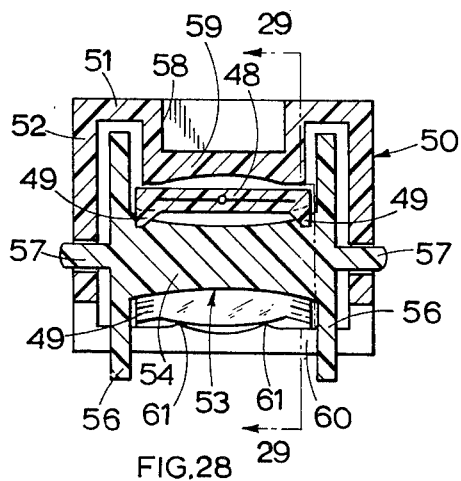
Figure 29:
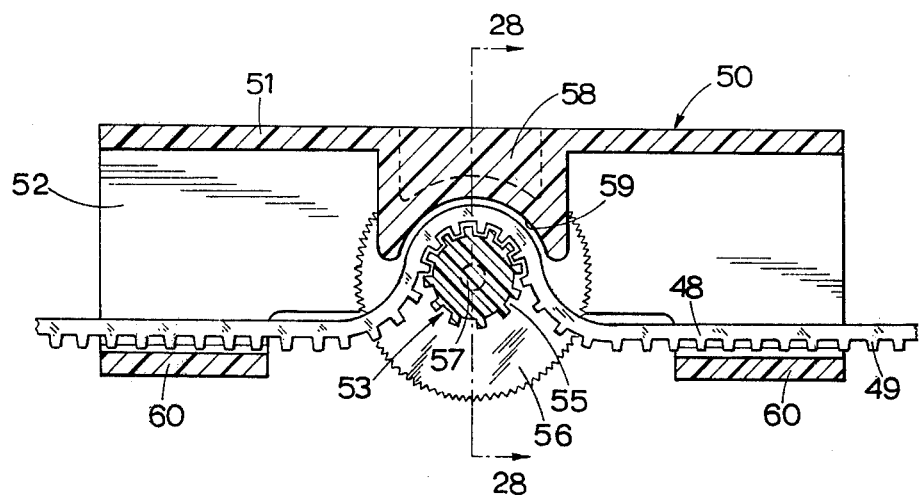

Embodiments of the present invention will now be described in greater detail, by way of example only, with reference to the accompanying drawings, in which:

FIG. 1 shows a tubular body intended to form part of a fluid flow control device in accordance with the present invention, FIGS. 2 to 6 are cross-sections of the body along the lines 2—2 to 6—6 of FIG. 1, respectively, FIGS. 7 to 10 are cross-sections of the body, corresponding respectively to FIGS. 3 to 6, showing each part of the body as it appears when kinked, FIG. 11 is a plan view of a tool used in the manufacture of the body shown in FIG. 1, FIG. 12 is a cross-section through a pair of dies used with the tool shown in FIG. 11 to manufacture a body of the kind shown in FIG. 1, FIG. 13 is a side view of a fluid flow control device in accordance with the invention and incorporating a tubular body of the kind shown in FIG. 1, FIG. 14 is a plan view of the device shown in FIG. 13, FIG. 15 is an end view of the device shown in FIG. 13, FIG. 16 is a section, to a larger scale, along the line 16—16 of FIG. 14, FIG. 17 is an end view of flexing means similar to that illustrated in FIG. 15 but incorporating a modification, FIG. 18 is a side view of flexing means similar to that shown in FIG. 13 but incorporating a further modification, FIG. 19 is a plan view of another form of flexing means for use with a tubular body of the kind shown in FIG. 1, FIG. 20 is a side view of the flexing means shown in FIG. 19, FIG. 21 is an end view of the flexing means as viewed from the right of FIG. 20, FIG. 22 is a section along the line 22—22 of FIG. 21, FIG. 23 is a section along the line 23—23 of FIG. 20, FIGS. 24 and 25 are sections similar to FIGS. 22 and 23 respectively, but showing the flexing means in another position of use, FIG. 26 is a perspective view of another form of device, FIG. 27 is a section, to a larger scale, along the line 27—27 of FIG. 26, FIG. 28 is a section, along the line 28—28 of FIG. 29, through yet another form of device, and FIG. 29 is a section along the line 29—29 of FIG. 28.

The flow control device shown in FIGS. 13 to 16 is intended for use in controlling the flow of a liquid such as blood or saline from a liquid container to a patient undergoing treatment. The device comprises a tubular body, shown in FIGS. 1 to 6, and flexing means.

The body is formed in part of a length of tube 10, the tube being of transparent PVC containing a relatively large porportion of plasticizer so that it is relatively flexible. In a typical construction the tube 10 has an outside diameter of slightly more than 5 mm and a wall thickness of slightly less than 1 mm.

The body includes a part of the tube which is shaped as shown. FIG. 2 is a section through an unshaped part of the tube. FIG. 3 is a section through part of the body which is flattened so that when the tube is flexed or kinked, as shown in FIG. 7 the opposite walls of the tube lie in contact with each other; this part of the body will be herein referred to as the closure portion 11. Beyond the closure portion 11 is a portion 12 of the body in which, when the tube is flexed or kinked, as shown in FIG. 8, the opposite walls again lie in contact with each other over most of their surfaces, but in which the walls are formed with complementary grooves 13 of tapered shape as can be seen from FIGS. 1, 4 and 5. Beyond the grooved portion 12 is a portion 14, herein referred to as the free-flow portion of the body, in which the body has opposed parallel walls which are permanently spaced apart, as shown in FIG. 6. Finally, beyond the free-flow portion 14 the tube is again of circular cross-section.

The body is shaped in the manner described and illustrated by being flattened between heated dies 15 and 16 (see FIG. 12), the dies being appropriately shaped along their lengths to give to the body the desired external shape. Before the tube is inserted between the dies, however, a tool of the kind having a tapered wire 17 projecting from a rectangular tongue 18. The tool has a handle 19 by means of which it can be withdrawn from the tube after the tube has been withdrawn from between the dies 15 and 16.

The flexing means is shown in FIGS. 13 to 16 and comprises a pair of parallel side plates 20 with three pins 21, 22 and 23 extending between them. The gap between the plates 20 is slightly wider than the width of the flattened portions 11, 12 and 14 of the tube. The pins are mutually parallel and are at right-angles to the plates. The central pin 22 constitutes the principal abutment, and the two outer pins 21 and 23 constitute formations operative to maintain the body in a flexed state. The principal abutment pin 22 is spaced at equal distances from the other two pins, but the pins do not lie in a common plane, the principal abutment pin 22 being displaced to one side of the plane containing the other two pins 21 and 23.

During assembly of the fluid control means the tube is threaded between the central pin 22 and one, 21, of the two outer pins, passed around that side of the central pin 22 remote from the plane containing the two end pins, and threaded back between the central pin 22 and the other, 23, of the two end pins. As can be seen in FIG. 16, a short length of the flattened part 11, 12 of the tube, adjacent to the central pin 22, is brought lightly into contact with the central pin and forms an arc 24 of about 90° around the central pin, the remaining parts of the tube extending from the arcuate part with their axes straight and substantially at right-angles to each other. It is found that the arcuate part 24 constitutes a kink in the tube such that the walls of the arcuate part are held together due in large part if not entirely to the internal stresses in the walls of the tube. As can be seen in FIG. 16 the walls of the tube are spaced apart except at the arcuate part 24. As the arcuate part 24 of the tube is a part of the portion 12 formed with grooves 13, liquid is able to pass through the grooves, and the rate of flow of the liquid is determined by the cross-section of the grooves in the arcuate part of the tube. If the flexing means is shifted longitudinally of the tube 10, so that the arcuate part of the tube has grooves of a different cross-section, the rate of flow of the liquid differs accordingly. The flow of liquid can be caused to cease entirely if the closure portion 11 of the tube is caused to form the arc, while the rate of flow of liquid can be increased very considerably if the free-flow portion 14 of the tube is caused to form the arc, the walls of that portion of the tube remaining in spaced relationship even when constrained to form an arc around the central pin 22.

Thus by varying the position of the flexing means along the flattened part of the tube the user can vary the rate of flow of liquid through the tube as required. To make it easier to vary the position of the flexing means the outside surfaces of the side plates 20 are preferably of slightly concave form and are ribbed or otherwise roughened to enable the flexing means to be readily gripped between the user's finger and thumb. It is often found, in fact, that only one hand is needed to adjust the position of the flexing means.

In order to reduce the likelihood of the walls of those parts of the tube that touch the end pins 21 and 23 from being brought into mutual contact and thereby further restricting or cutting off the liquid flow, those end pins may be modified as illustrated in FIG. 17. Here the end pins 21 and 23 are replaced by end pins 25 bent into shallow curves, the concave sides of which receive the adjacent walls of the tube as they bow out due to the pressure of the liquid in the tube or due to the innate tendency of the tube to open out.

In a modified construction shown in FIG. 18 the flexing means is made as a unitary moulding of a plastics material such as nylon or polypropylene. Instead of pin-like rods there are transverse walls or septae 26 and 27 such that their end edges 28 and 29 perform the same functions as the pins. There is a central septum 26 with a straight edge 28 around which the flattened part of the tube can be bent into arcuate shape, and two end septae 27 with concave edges 29 for locating parts of the tube on either side of the arcuate part.

If the flow control means has been left in one position of adjustment for an extended period of time the arcuate part of the tube may become set. To overcome that difficulty it is usually only necessary to move the flexing means to and fro a few times along the tube so as to cause repeated straightening and flexing of the previously arcuate part.

In the embodiment shown in FIG. 18, however, the arrangement is such that the tube can be removed from between the septae 26 and 27 so that it can straightened out and will not become set. In addition, even if no free-flow portion 14 is provided, removal of the tube from the flexing means enables liquid to flow freely through the tube. To enable the tube to be removed a slot 30 is formed in one of the side plates 20 through which the flattened part of the tube can be manipulated. In a modification (not illustrated) one of the side plates is largely or wholly omitted. Alternatively the side plates 20 are complete (that is without slots) and one of the end pins or septae may extend only part way from one side plate towards the other, the gap between the end of the pin or septum and the other side plate being wide enough to enable the user to manipulate the flattened part of the tube through the gap. If both the end pins or septae are formed in that manner the tube can be completely detached from the flexing means.

A tubular body of the kind shown in FIG. 1 may also be used with the flexing means shown in FIGS. 19 to 25. The flexing means is made as a unitary moulding from a plastics material which is flexible and resilient but which is relatively stiff so that a siginificant force must be exerted to cause its flexure. The flexing means can be made with a simple two-part mould, as will be appreciated from a study of the drawings.

The flexing means comprises a pair of spaced plates 31 and 32 of approximately rectangular shape in plan (FIG. 19) but bowed away from each other as can be seen in FIG. 20. The corners of the plates are interconnected by integral corner posts 33 which with the ends of the plates define inlet and outlet openings for the tubular body. The upper plate 31 carries a supporting bar 34 which depends from the middle of one of its longer edges. An arm 35 constituting the principal abutment projects from the lower end of the supporting bar so as to lie about half way between the plates 31 and 32 and to extend in a direction substantially parallel with the shorter sides of those plates. The upper surface of the arm 35 is curved in cross-section as can be seen in FIG. 22, but in longitudinal section, as shown in FIG. 23, the uppermost part of the arm presents a straight edge not parallel with the plates 31 and 32 but slightly inclined relative to those plates.

Supporting bars 36 similar to the supporting bar 34 project upwards from the lower plate 32; but the bars 36 are on the opposite side of the flexing means from the bar 34 as will be seen from FIGS. 19 and 21. Arms 37 project from the upper end of the bars 36 and are parallel with and generally similar to the arm 35, though inverted. As can be seen from FIGS. 20 and 22 the arms are curved in cross-section like the arm 35. Unlike the arm 35, however, the arms 37 are not straight in longitudinal section but are of concave shape as can be seen in FIGS. 21 and 25.

For simplicity of illustration the tubular body is not illustrated, but when assembled with the flexing means it passes through the inlet opening at one end, beneath the first of the arms 37, above the principal abutment arm 35, beneath the other of the arms 37 and through the outlet opening. The three arms act like the pins 22 and 25 shown in FIGS. 16 and 17, and that part of the tubular body passing round the arm 35 forms a kink like the kink 24. It will be appreciated, though, that as the edges of the arms engaged by the tubular body are slightly inclined, as described above, the main flat faces of the tubular body are inclined slightly to the main faces of the upper and lower plates 31 and 32.

If it is desired to allow liquid to flow freely through the tubular body the upper and lower plates 31 and 32 can be squeezed towards each other so that they become substantially planar as shown in FIGS. 20 and 21. This causes the arms 35 and 37 to adopt the positions illustrated so that the tubular body can now straighten out, the kink is removed and the liquid can flow without restriction. An advantage of this arrangement is that when the flexing means has been set to achieve a desired rate of flow and it is temporarily desired to permit the free flow of liquid this can be achieved by squeezing the plates 31 and 32, and when the plates are subsequently released the former flow rate is restored again. Another advantage is that there is no need to use a tubular body having a free flow portion 14.

FIGS. 26 and 27 illustrate a form of flexing means somewhat like those shown in FIGS. 13 to 18 but including mechanism enabling the user to move the flexing means smoothly and accurately along the tubular body using only one hand. The flexing means has side plates 38 and end septae 39 with concave lower edges. The principal abutment, between the septae 39 is afforded by a roller 40 mounted between the side plates 38 for free rotation. The central part of the roller is smooth but the parts 41 adjacent to the side plates are knurled, ribbed or otherwise shaped to engage frictionally the marginal parts of the flattened portion 42 of the tubular body 43, this tubular body resembling that shown in FIG. 1.

A drive roller 44 is mounted above the roller 40 and has a smooth central part, and shaped parts 45 similar to the shaped parts 41 of the roller 40. The ends of the drive roller 44 carry thumb-wheels 46 which project above the edges of the side plates 38 and are knurled or otherwise roughened to enable them to be readily rotated. The side plates 38 are extended to provide handles 47 which can be grasped in one hand while the thumb is used to rotate the thumb-wheels 46.

The tubular body extends between the rollers 40 and 44 and is marginal parts and frictionally engaged between the end parts 41 and 45 of the rollers so that rotation of the drive roller 44 causes the flexing means to move along the tubular body 43.

It will be appreciated that as the part of the flattened portion 42 that passes over the roller 40 forms an arc like the arc 24, the walls of that part are held in mutual contact due to the internal stresses set up in the body arising from the flexure of the body into an arcuate shape. Thus the roller 40 acts as the principal abutment. The driver roller 44 has no significant part to play in holding the walls in contact, particularly in the neighbourhood of the grooves. The smooth central part of the drive roller 44 is shown as being of reduced diameter in order to emphasize the fact that it plays no part in holding the walls together. In practice, however, the central portion may be similar to that of the lower roller 40. In a modified arrangement (not illustrated) the roller 40 does not act as the principal abutment, and the rollers engage a straight part of the tube to one side of the principal abutment.

FIGS. 28 and 29 illustrate another form of device enabling the user to move the flexing means relatively to the body using only one hand. The body, 48, largely resembles the body shown in FIGS. 1 to 6, but the flattened part of the body is formed along its margins with teeth 49 of triangular shape. The teeth are formed during the shaping process described above with reference to FIG. 12, the die 15 being formed with appropriate recesses into which the heated material flows to form the teeth.

The flexing means comprises a unitary frame 50 of plastics material including a back plate 51 with spaced parallel side plates 52, and additionally comprises a unitary rotor 53 also of plastics material. The central part 54 of the rotor 53 is slightly waisted as shown, and at its ends is formed with recesses 55 to accommodate the teeth 49 on the body. Beyond the central part 54 of the rotor are thumb-wheels 56 with roughened or grooved rims, and beyond the thumb-wheels are trunnions 57 which enter aligned bearing holes in the side plates 52.

A guide 58 projects from the back plate 51 and includes a curved plate 59 co-axial with the rotor 53. The body 48 extends in an arc around the central part 54 of the rotor and is held in position by the marginal parts of the curved plate 59, the central part thereof being slightly grooved or hollowed out as can be seen in FIG. 28. The body thus forms a kink around the rotor so that the walls of the flattened part of the body are held in contact as shown in FIG. 28. Those parts of the body 48 at either end of the kinked part are gently curved, the curvature being insufficient to kink the body. The body is held in this gently curved shape by fixed guide plates 60 constituting integral parts of the frame 50, the guide plates having spaced rails 61, as shown in FIG. 28, for engaging those parts the body immediately adjacent to the teeth 49. Those parts of the body projecting from the ends of the frame are in substantial alignment with each other.

In use the user can hold the frame 50 in his or her hand and can rotate the thumb-wheels with the thumb of that hand thereby causing the body to move longitudinally relative to the flexing means.

In a modified construction (not illustrated) the trunnions 57 enter slots in the side plates 52. The trunnions are normally held at the ends of the slots, in positions corresponding to those illustrated in FIG. 28, by resilient means or catch means, but can be moved along the slots in a direction away from the guide 58 so that the body is no longer kinked around the rotor 53 and its walls can part to allow the free flow of fluid.

Many of the embodiments illustrated are described as if they were in particular positions or orientations; for example some parts are described as upper or lower. It is to be understood however that this has been done to simplify the description and that the flow control devices concerned may be used in any desired positions or orientations.

Further, the tubular bodies illustrated are all such that in the absence of other forces the walls of the flattened portions thereof tend to lie somewhat apart from each other in mutually spaced relationship, as shown in FIGS. 3 to 5. It is to be understood, though, that they could equally well be replaced by tubular bodies differing from them solely in the fact that when they are unstressed the walls of the flattened portions thereof tend to lie together in mutual contact with each other; the fluid pressure causing them to separate in use, except in the localised area of the kink. The flattened portions of such a body when unstressed would appear in cross-section like FIGS. 7 to 10.

I claim:

1. Means for controlling fluid flow comprising a body defining a passageway having opposed flexible walls which for at least a portion of the axial length of the body are capable of being held in mutual contact throughout their cross-section except for a limited region, this region being a cross-sectional flow area which varies along the general direction of flow through the passageway, and flexing means operative to retain the body in a predetermined flexed state such that the walls are held in contact, over a localised area of limited axial length, due at least in part to the internal stresses set up in the body arising from the flexure of the body rather than to external clamping forces applied to the opposite sides of the walls immediately adjacent to said area, said flexing means being arranged that said body can be moved lengthwise relative to the flexing means so as to alter the position of said localised area while the body is maintained in said flexed state.

2. Means for controlling fluid flow, according to claim 1, in which the limited region in which the walls do not come into contact is deformed by a tapered groove in at least one of the walls.

3. Means for controlling fluid flow, according to claim 1, in which the body includes a closure portion having flexible walls capable of being retained in mutual contact throughout their entire cross-section when said closure portion is retained in said predetermined flexed state by the flexing means, the arrangement being such that said localised area of limited length can be transferred to the closure portion whereupon the flow of fluid through the passageway is prevented.

4. Means for controlling fluid flow, according to claim 1, in which the flexing means defines a path for the body such that it is retained in a flexed state, said localised area comprising part of the body flexed transversely of the body.

5. Means for controlling fluid flow, according to claim 4, in which the flexing means includes first and second formations on one side of said path and operative to locate spaced portions of the body, and a principal abutment located between said formations and on the other side of said path, the body being constrained so that part thereof is curved around the principal abutment and the walls of this curved part of the body are held in contact, the curved part thus comprising said localised area of limited axial length.

6. Means for controlling fluid flow, according to claim 5, in which said formations present concave faces towards said path whereby the separation of the walls of the body adjacent to the formations is not restrained as much as it would be if the formations presented flat faces towards said path.

7. Means for controlling fluid flow, according to claim 5, in which there is an opening laterally of the path at least on one side of the principal abutment whereby that part of the body adjacent to the opening can be moved through the opening and freed from the adjacent formation and the body can assume a less curved shape so that the walls thereof are no longer held in contact over said localised area by the internal stresses in the body arising from flexure of the body.

8. Means for controlling fluid flow, according to claim 5, in which the principal abutment is movable relatively to at least one of said formations whereby the body can assume a less curved shape so that the walls thereof are no longer held in contact over said localised area by the internal stresses in the body arising from flexure of the body.

9. Means for controlling fluid flow, according to claim 5 in which there is manually operable drive means comprising at least one rotatable drive member which co-operates with the body in such a manner that when the drive means is rotated the body moves lengthwise along said path.

10. Means for controlling fluid flow, according to claim 9, in which said rotatable drive member constitutes said principal abutment.

11. Means for controlling fluid flow, according to claim 10, in which the body and the rotatable drive member constituting the principal abutment are provided with mutually interengaging formations whereby rotation of that drive member causes positive longitudinal movement of the body.

12. Means for controlling fluid flow, according to claim 11, in which said interengaging formations comprise integral teeth formed along the marginal parts of the body and complementary recesses formed in the rotor constituting the principal abutment.

13. Means for controlling fluid flow according to claim 1 wherein the body defining the passageway comprises a hollow tubular member, a longitudinally extending flattened portion in said member, the opposed walls of said flattened portion being normally spaced apart to define said passageway in said flattened portion, said flexing means being operative upon the walls of said flattened portion.

* * * * *